(12) United States Patent
Songer

(10) Patent No.: US 7,090,675 B2
(45) Date of Patent: Aug. 15, 2006

(54) SYSTEM AND METHOD FOR BONE FIXATION

(75) Inventor: Matthew N. Songer, Marquette Township, MI (US)

(73) Assignee: Pioneer Laboratories, Inc., Marquette, MI (US)

( * ) Notice: Subject to any disclaimer, the term of this patent is extended or adjusted under 35 U.S.C. 154(b) by 0 days.

(21) Appl. No.: 10/809,248

(22) Filed: Mar. 25, 2004

(65) Prior Publication Data
US 2004/0181225 A1 Sep. 16, 2004

Related U.S. Application Data

(62) Division of application No. 10/007,146, filed on Dec. 3, 2001, now Pat. No. 6,730,092.

(51) Int. Cl.
*A61B 17/58* (2006.01)
(52) U.S. Cl. .......................................... 606/61; 606/73
(58) Field of Classification Search ................ 606/61, 606/72–74, 103, 104, 86
See application file for complete search history.

(56) References Cited

U.S. PATENT DOCUMENTS

| | | |
|---|---|---|
| 5,156,616 A | 10/1992 | Meadows |
| 5,456,685 A | 10/1995 | Huebner |
| 5,456,722 A | 10/1995 | McLeod et al. |
| 5,534,011 A | 7/1996 | Greene, Jr. |
| 5,540,703 A | 7/1996 | Barker, Jr. et al. |
| 5,571,139 A | 11/1996 | Jenkins, Jr. |
| 5,611,801 A | 3/1997 | Songer |
| 5,628,757 A | 5/1997 | Hasson |
| 5,702,399 A | 12/1997 | Kilpela et al. |
| 5,707,395 A | 1/1998 | Li |
| 5,951,560 A | 9/1999 | Simon et al. |

(Continued)

OTHER PUBLICATIONS

Photographs of a prior art vertebral stabilization system employing a cable extending through projecting heads of a screw anchor.

*Primary Examiner*—Eduardo C. Robert
*Assistant Examiner*—D. Jacob Davis
(74) *Attorney, Agent, or Firm*—Fitch, Even, Tabin & Flannery

(57) ABSTRACT

A system and method for maintaining positions of bones fixed or approximated relative to each other is provided that is ideal for minimizing interference with surrounding viscera in spinal column procedures, although other good applications therefor are also disclosed. In the preferred form, a cable anchoring apparatus in the form of a screw member having an elongate shank that is threaded for substantially the full length thereof is employed. An internal driver surface is provided so that the size of the proximate end of the shank can be minimized or maintained consistently sized with respect to the reminder of the shank with no enlarged driver head formed thereat. This allows the amount of bone material that is removed from full insertion of the screw anchor to be minimized, i.e. no countersinking for an enlarged driver head is necessary, thus improving holding power of the cable anchor herein. Further, the full threading of the shank for substantially its entire length enables the screw member to be fully sunk into the bone so that no portions thereof, such as an enlarged screw head, project into the surrounding body cavity in which the bone is located. In the spinal column application, a criss-cross cable pattern is disclosed to better resist torsional forces and keep any decompression devices in place in the gap between adjacent vertebrae.

7 Claims, 5 Drawing Sheets

U.S. PATENT DOCUMENTS

| | | |
|---|---|---|
| 5,989,256 A | 11/1999 | Kuslich et al. |
| 6,033,429 A | 3/2000 | Magovern |
| 6,241,736 B1 | 6/2001 | Sater |
| 6,248,106 B1 | 6/2001 | Ferree |
| 6,283,973 B1 | 9/2001 | Hubbard et al. |
| 6,293,961 B1 | 9/2001 | Schwartz |
| 6,325,802 B1 | 12/2001 | Frigg |
| 6,387,129 B1 | 5/2002 | Rieser et al. |
| 6,423,065 B1 | 7/2002 | Ferree |
| 2001/0041916 A1* | 11/2001 | Bonutti ............ 606/232 |
| 2002/0120270 A1* | 8/2002 | Trieu et al. ......... 606/61 |
| 2003/0065361 A1* | 4/2003 | Dreyfuss ........... 606/232 |

* cited by examiner

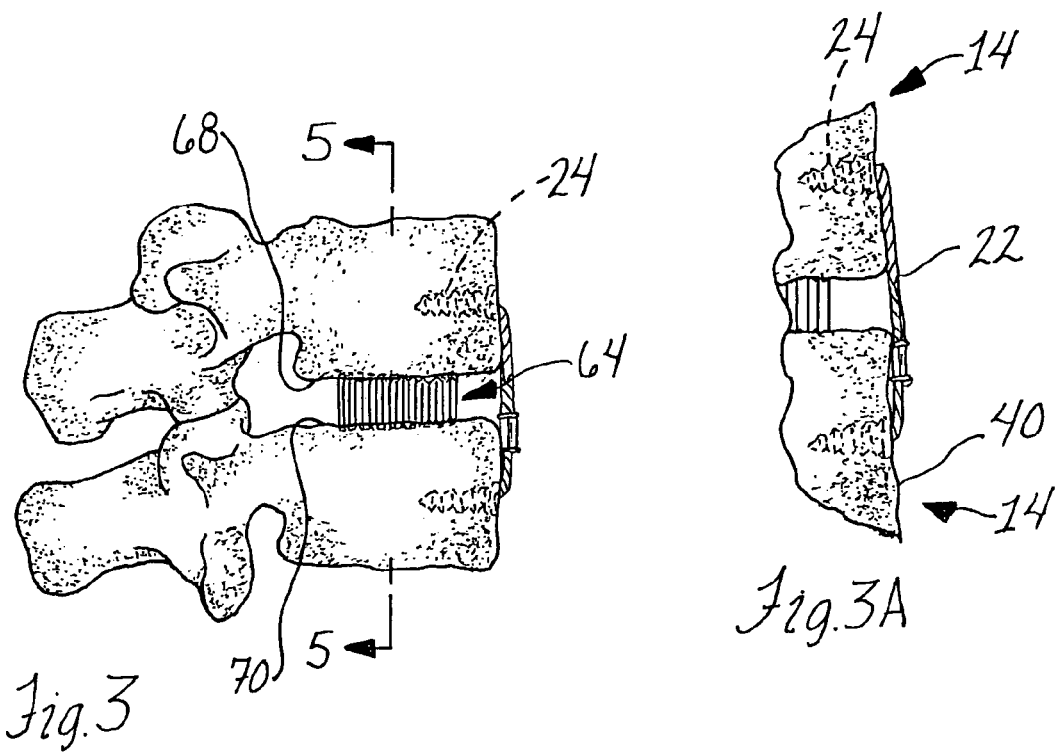
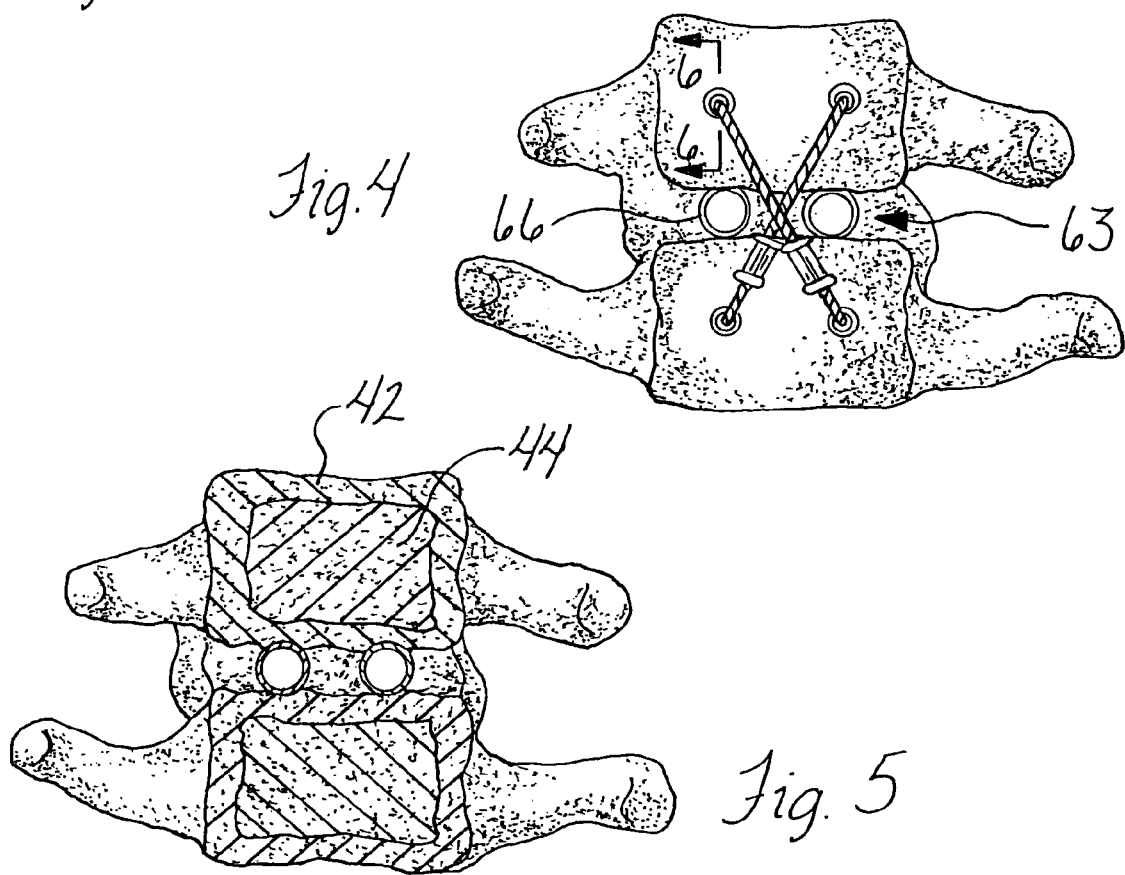

SYSTEM AND METHOD FOR BONE FIXATION

CROSS REFERENCE TO RELATED APPLICATION

This is a division of prior application Ser. No. 10/007,146, filed Dec. 3, 2001 now U.S. Pat. No. 6,730,092, which is hereby incorporated herein by reference in its entirety.

FIELD OF THE INVENTION

The invention relates to a bone fixation system and method and, more particularly, to a cable anchoring apparatus for using cables to stabilize bones relative to each other.

BACKGROUND OF THE INVENTION

It is known to use cables anchored to bones for various medical procedures. For example, with respect to the spinal column, several applications are apparent. However, one significant limitation with these applications is the need for posterior procedures, particularly where anterior procedures would be preferable, but whose performance is limited by the space required of current cable anchors in the body cavity. Anterior along the spinal column are significant impediments to having cable anchor members projecting from the vertebrae in which they are sunk such as surrounding viscera including organs, intestines and large blood vessel groupings. Another problem is the toggling effect projecting anchors can create with tensioned cables extending transverse thereto and thus generating a bending movement at the projecting anchor head.

Accordingly, there is a need for an improved cable bone fixation system, and particularly a system and method that allows for cables to be anchored anteriorly along the spinal column with potential for interference with surrounding viscera minimized.

SUMMARY OF THE INVENTION

In accordance with the present invention, a system and method for maintaining positions of bones fixed or approximated relative to each other is provided that is ideal for minimizing interference with surrounding viscera in spinal column procedures, although it will be recognized its use is not so limited as the robust and secure anchoring provided thereby will be desirable in many bone fixation procedures. In the preferred form, a cable anchoring apparatus in the form of a screw member having an elongate shank that is threaded for substantially the full length thereof is employed. An internal driver surface is provided so that the size of the proximate end of the shank can be minimized; in other words, the shank proximate end is maintained consistently sized with respect to the reminder of the shank, i.e. no enlarged driver head is formed thereat. This allows the amount of bone material that is removed from full insertion of the screw anchor to be minimized, i.e. no countersinking for an enlarged driver head is necessary, thus improving holding power of the cable anchor herein. Further, the full threading of the shank for substantially its entire length enables the screw member to be fully sunk into the bone so that no portions thereof, such as an enlarged screw head, project into the surrounding body cavity in which the bone is located.

A flexible cable is attached to the screw to be anchored to the bone and for being attached to another anchored cable so that surfaces of bones or bone portions having the cables anchored thereto can be approximated in fixed position relative to each other. Also, with the screw anchors fully sunk into the bones, the cables are able to ride on the bone surfaces to provide them with a large bearing surface along their length so as to minimize points of stress concentration therealong and the potential for wear these create.

Herein, it will be understood that the terms bones or bone portions are interchangeable and can refer to distinct bones such as vertebrae in a spinal column or portions of a single vertebrae bone or other bone. Generally, in the single bone aspect, the surfaces to be approximated are those at the fracture, whereas with distinct bones, it is the facing surfaces of the bones which are the surfaces that are desired to be held in substantially fixed positions relative to each other despite dynamic motion of the body part, e.g. spinal column, that they support.

In terms of procedures or indications in which the cable anchor apparatus herein can be used, one typical procedure is in conjunction with intervertebral decompression devices such as an adjunct to a cage or barrel used to support adjacent vertebrae in a fixed, spaced position relative to each other. The preferred spinal levels of use are L5 (fifth lumbar vertebra)—S1 (adjacent sacrum bone) and L4 (fourth lumbar vertebra)—L5. In this application, two screw anchors can be inserted into each bone portion with the cables thereof interconnected by connectors such as crimp connectors so that the cables form a criss-cross cable pattern as they extend across the gap between the two vertebrae with the cage or cages therebetween. The criss-cross cable pattern provides increases resistance against the torsional forces that the spinal column generally creates during dynamic motion thereof so as to keep the facing vertebrae surfaces approximated and minimizes motion of these surfaces that can be detrimental to proper healing and the healing process itself. In this regard, the cross-cables also tend to minimize the tendency for the decompression cages to back out of the space between the vertebrae with motion of the spinal column.

The cable anchoring system herein can also be used laterally on the spine such as for reducing scoliosis. Depending on the curvature of the spine to be corrected, the cable anchors are applied into two adjacent vertebrae with the cables thereof tensioned and crimped together via the crimp connector to apply a counteracting force against the curvature toward a straightening of the spinal column. In a pubis symphysis fracture, the cable screw anchor is inserted into each pubis, and the cables are then connected. In addition to anterior spinal stabilization such as with the above-described multiple pairs of cable screw anchors having their associated cables connected and tensioned in a criss-cross fashion, lateral spinal stabilization can also be accomplished with the present cable screw anchors. The cable screw anchors can also be used for posterior spinal stabilization such as to secure a laminar fracture. Each cable screw anchor is screwed into the pedicle on each side of a spinous process. The tensioned cables pull the fractured part of the vertebra into position for proper healing to occur.

BRIEF DESCRIPTION OF THE DRAWINGS

FIG. 3 is an enlarged side elevational view of the adjacent vertebrae showing the cables anchored to the vertebrae bone by screw anchors that are sunk into the bone to be substantially flush to the surface thereof;

FIG. 3A is a fragmentary view of the screw anchors and cables of FIG. 3 showing the cables riding on the bone surfaces;

FIG. 4 is an enlarged front elevational view of the anchored cables configured in a criss-cross pattern for stabilizing adjacent vertebrae in fixed positions relative to each other showing crimp connectors for attaching the cables together;

FIG. 5 is a cross-sectional view taken along line 5—5 of FIG. 3 showing a pair of decompression cages disposed between the adjacent vertebrae to maintain a desired spacing between the facing surfaces thereof;

DETAILED DESCRIPTION OF THE PREFERRED EMBODIMENTS

Figure 1:
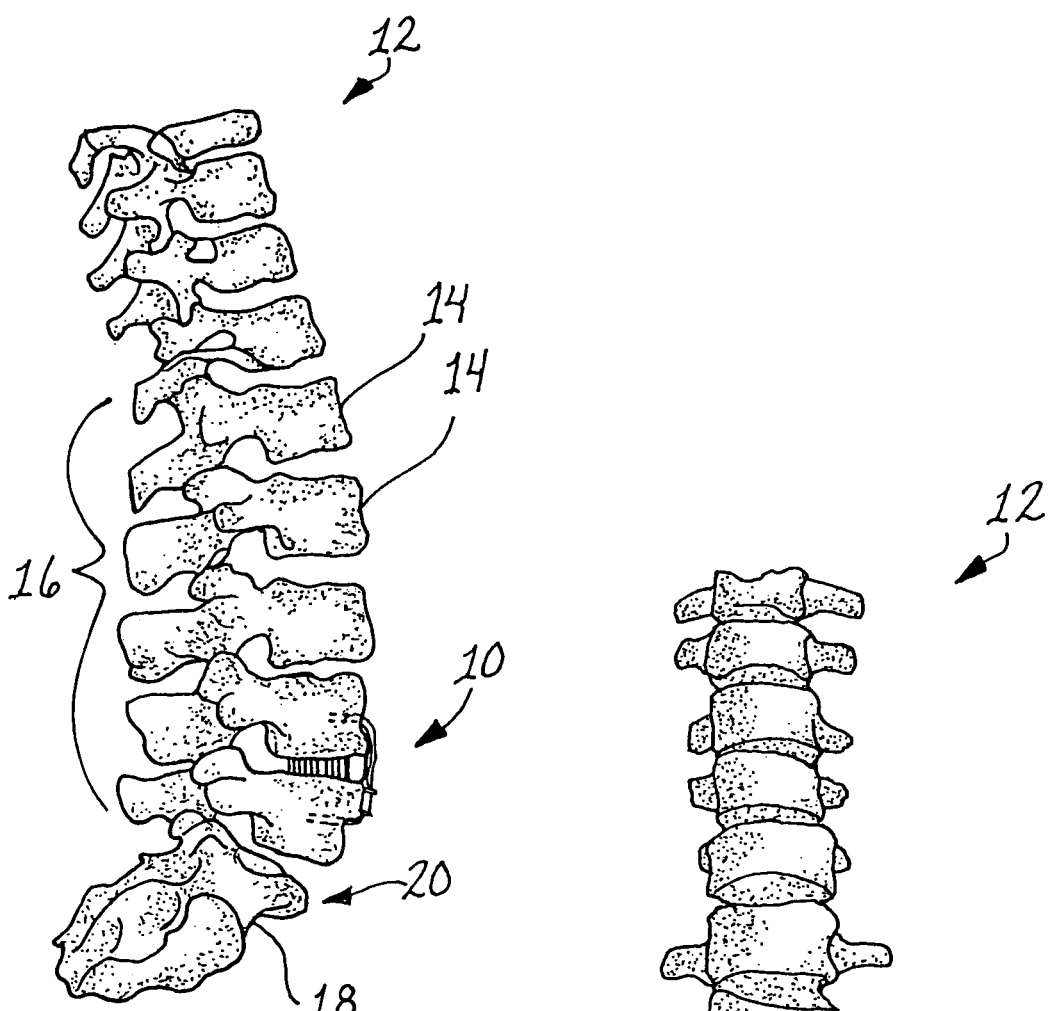
FIG. 1 is a side elevational view of a bone fixation system in accordance with the present invention shown applied to adjacent vertebrae in a spinal column.
Figure 2:
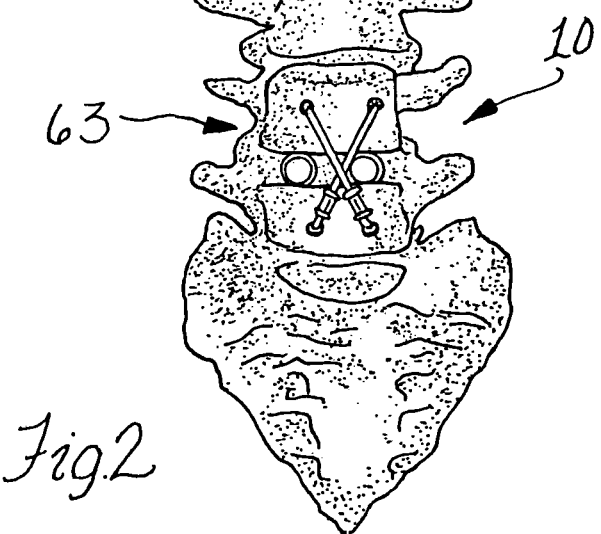
FIG. 2 is a front elevational view of the spinal column of FIG. 1 showing the cable bone fixation system having cables configured in a criss-cross pattern.

In FIGS. 1 and 2, a bone fixation system 10 is shown used on the spinal column 12, and more particularly on vertebrae bones 14 in the lower lumbar region 16 of the spine 12. The system 10 in typical usage is applied to the vertebrae bones 14 of the lower lumbar region 16, such as between the L4 and L5 vertebrae 14 as illustrated, as well as between the composite vertebrae bones 18 in the sacrum region 20 of the spinal column 12, i.e. the L5 and S1 vertebrae bones.

Figure 7A:
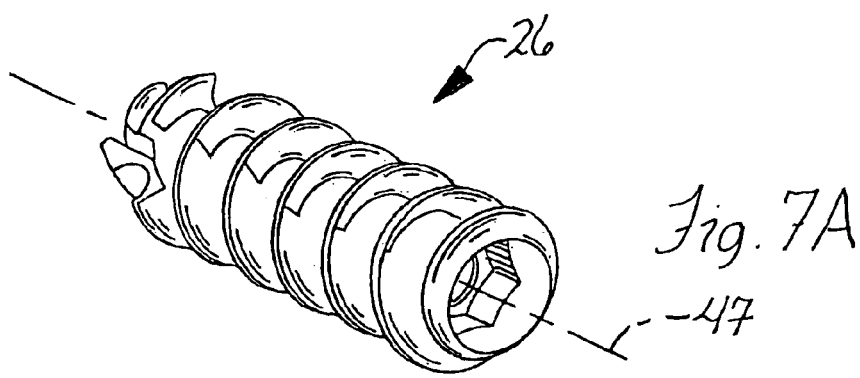
FIG. 7A is a perspective view of the cable screw anchor showing an internal hex driver surface formed at the proximate end of the screw shank.
Figure 7B:
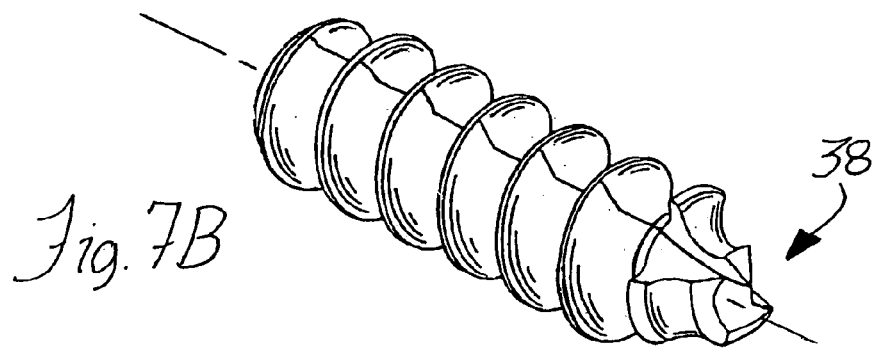
FIG. 7B is a perspective view of the cable screw anchor showing a point formed at the distal end of the screw shank for self-tapping of the screw.
Figure 8:
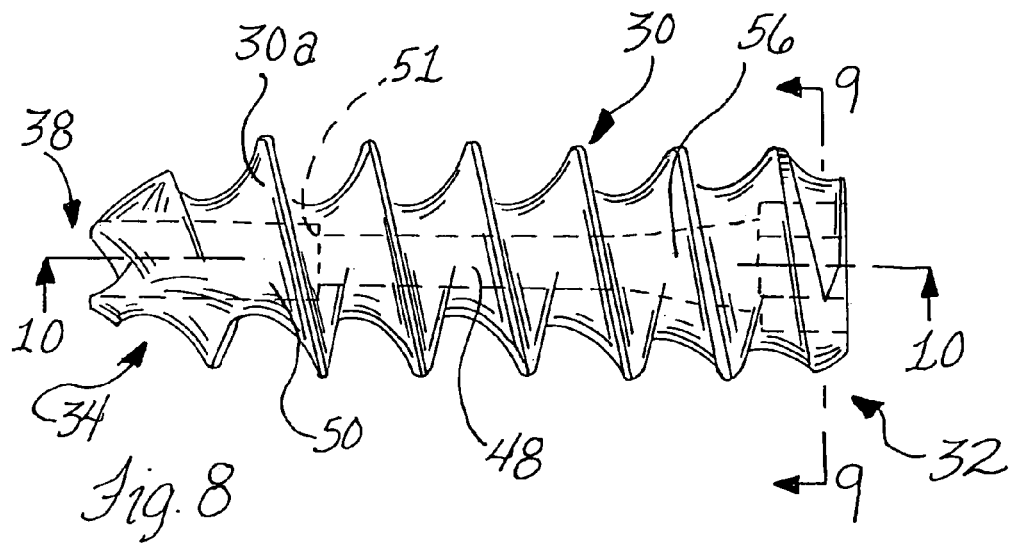
FIG. 8 is a side elevational view of the screw showing threads for substantially the full length of the shank.
Figure 10:
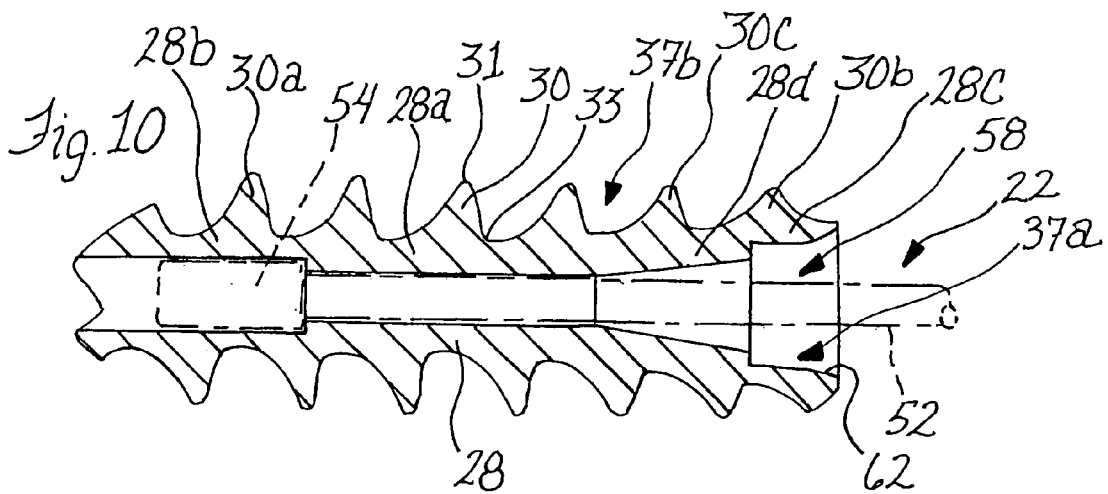
FIG. 10 is a cross-sectional view taken along 10—10 of FIG. 8 showing a cable in phantom secured in the throughbore of the shank via a counter-bore shoulder surface at the distal end of the shank and an enlarged plug portion at the corresponding end of the cable.

The bone fixation system 10 herein utilizes flexible cables 22 that are secured to the bones 14 by anchor members 24 (FIG. 3), preferably in the form of screw anchors 26, as shown in FIGS. 7A and 7B. The screw anchors 26 include a shank 28 preferably of a cancellous material and that is threaded with external threads 30 for substantially its entire length from the proximate end 32 to the distal end 34 thereof, as can be seen in FIGS. 8 and 10. In this regard, the screw anchors 26 are preferably headless and can be provided with an internal driving surface 36 along an internal surface thereof generally designated 37a and an outer surface generally designated 37b along which the threads 30 are formed. The internal driver surface 36 is preferably formed to be disposed adjacent the shank proximate end 32 with the distal end 34 forming a point configuration 38 thereat. As shown in FIGS. 7A, 7B and 8, the point configuration 38 has a split construction and the threads 30 are provided with an aggressive pitch and major/minor diameter configuration to provide the screw anchors 26 with a self-tapping ability, as will be described more fully hereinafter.

Figure 6:
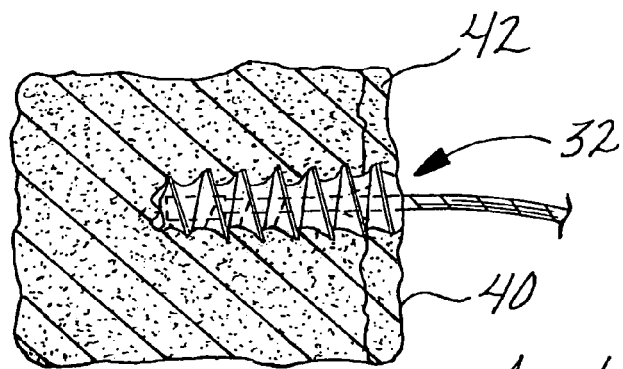
FIG. 6 is a cross-sectional view taken along line 6—6 of FIG. 4 showing the screw anchor fully sunk into the vertebrae bone so that it is flush with the bone surface at its proximate end.

With the preferred and illustrated fully threaded and headless screw anchor members 26 herein, they can be fully sunk into the bone 14 so that their proximate ends 32 lie substantially flush with bone surface 40 as shown in FIG. 6, or recessed therebelow if desired. This aspect of the present invention is of particular value in the aforedescribed spinal column procedures utilizing the present bone fixation system 10. To this end, because the screw anchors 26 can be sunk so that they do not project beyond the bone surface 40, the present bone fixation system 10 utilizing the preferred screw anchors 26 herein allow for anterior procedures to be performed on the spinal column 12 with interference with surrounding viscera substantially minimized. In addition, toggling effects as can be created by the tensioned cables 22 pulling on the screw anchors 26 in directions transverse to the length thereof is substantially minimized by having the cables 22 bearing on the bone surface 40 due to the full sinking of the screw anchors 26 in the bone 14. In other words, instead of having the cables 22 pulling on an enlarged head of an anchor projecting beyond the bone surface 40 such that the cables 22 are spaced therefrom with the bending moment this creates at the projecting head, the present bone fixation system utilizing the fully sunk anchor members 24 has these forces distributed along the length of the cable 22 in engagement with the bone surface 40 as well as within the screw shank 28, as described hereinafter.

Bones 14 generally have an outer cortex material 42 that is stronger than the inner material 44 (FIG. 5) thereof so that the cables 22, which are typically of stainless steel or titanium strand material, have a durable surface against which they bear for minimizing wear of the cables 22. The headless screw anchors 26 herein keep the size of their proximate ends 32 to a minimum relative to headed screws so that there is no need to countersink the bone 14 near the surface 40 thereof to enable the present screw anchors 26 to be fully inserted in the bone 14. Because the screw anchors 26 have substantially the same external size or configuration along their entire length less the reduced size end point 38 thereof, excess bone material need not be removed for the shank end 32 over that needed to accept the remainder of the screw shank 28. In this way, with the screw anchors 26 inserted to full depth in the bone 14, the amount of the hard cortex material 42 of the bone 14 adjacent the bone surface 40 surrounding the shank end 32 is maximized to provide increased surrounding bone support and especially with the strongest part of the bone at the screw end 32 so that the screw anchors 26 have improved levels of holding power and reduced toggling considerations.

Figure 9:
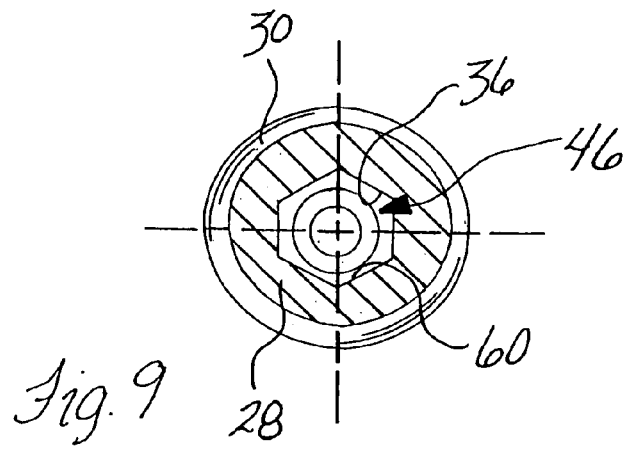
FIG. 9 is a cross-sectional view taken along 9—9 of FIG. 8 showing the peripheral surface configuration of the axial throughbore formed through the length of the screw shank.

Referring next to FIGS. 8–10, it can be seen that in the preferred form, the screw anchor 26 is cannulated as by including a lumen or throughbore 46 that extends through the screw shank 28 along the central axis 48 thereof and which opens at both shank ends 32 and 34. The cables 22 can be secured to their screw anchors 26 in any number of ways. As shown, the throughbore 46 has a main, small diameter, intermediate section 48 which opens to a larger counterbore section 50 having a larger diameter at distal end 34 of the screw shank 28, as can be seen in FIGS. 8 and 10. A stop surface in the form of an annular shoulder surface 51 is formed between the main and counterbore sections 48 and 50 of the throughbore 46. The flexible cables 22 include a flexible elongate portion 52 having an enlarged plug portion 54 at the rear end thereof so that upon threading the cable 22 through the throughbore 46 of the screw shank 28, the plug portion 54 will abut against the shoulder surface 51.

The throughbore 46 is also configured to minimize discrete stress points on the cable 22 and specifically the elongate flexible portion 52 thereof. In this regard, the main section 48 has a tapered portion 56 thereof where the surface of the throughbore 46 tapers or flares outwardly relative to the axis 48 as it progresses toward the proximate end 32 of the screw shank 28. Since the cable 22 will be pulled in a direction transverse to the length of the shank 28 along its axis 47, and specifically in a direction substantially perpendicular thereto when connected in tension to another anchored cable 22, the tapered portion 56 of the throughbore section 48 allows the cable 52 to begin to flex in the direction it is to undertake when exiting from the bore 46 at the proximate end 32 of the shank 28.

Figure 11:
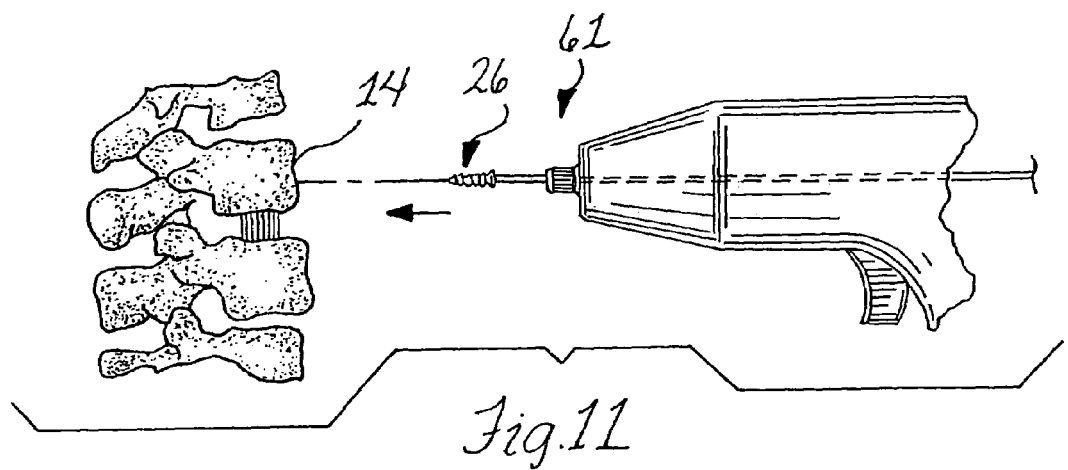
FIGS. 11–13 show the installation procedures for inserting the cable screw anchors into the vertebrae bones, and connecting and crimping the cables across adjacent vertebrae to form the criss-cross pattern thereof.

As previously mentioned, the driver surface 36 is preferably formed adjacent the shank proximate end 32. For this purpose, the tapered throughbore portion 56 opens to an enlarged counterbore section 58 formed at the end of the throughbore 46. The counterbore portion 58 provides an opening at the proximate end 32 of the shank 28 and is provided with a hex-shaped peripheral surface 60 for driving engagement with a correspondingly configured driver such as can be included in the cannulated power-driven tool 61 depicted in FIG. 11. Cannulated hand drivers can also be utilized. Again, in the interest of minimizing stresses along the flexible cable portion 52, the outermost edge of the hex surfaces 60 are radiused at 62 so that when the cable 22 is bent thereabout, it is not exposed to any sharp edges that can create points of weaknesses therein with the cable tensioned and set in this fashion which can span significant lengths of time, e.g. several months, to achieve the necessary healing, i.e. bone union or fusion, before the fixation system 10 herein can be removed.

Accordingly, as can be best seen in FIG. 10, the wall thickness of the shank 28 between the inner and outer surfaces 37a and 37b thereof varies along the shank length, with its maximum thickness extending along the majority of its length at 28a, i.e. along the main bore section 48. The shank 28 has thinner wall sections 28b–28d toward the proximate and distal ends 32 and 34 thereof due to the presence of the counter bores 50 and 58, and the tapered bore portion 56, with the lengths thereof being minimized to have little to no effect on the robust holding power provided by the present screw anchors 26 when screwed into bones 14. To this end, only a single full-sized thread 30a is generally radially aligned with the counterbore 50, and a single thread 30b is generally radially aligned with counterbore 58. Four threads 30 are disposed on the thicker wall portion 28a of the shank 28, with only one thread 30c thereof formed on the gradually thinning wall portion 28d so as to be generally radially aligned with the tapered bore portion 56. In this manner, the majority of the threads 30 with respect to any of the wall portions 28a-28d are formed on the cannulated screw anchor 26 at the shank wall portion 28a where it is thickest to maximize the strength of the externally threaded shank wall and the holding power provided thereby when screwed into a bone 14.

Continuing reference to FIG. 10, the preferred configuration of the screw anchor 26 will next be described. By way of example and not limitation, the length of the screw shank 28 between the ends 32 and 34 thereof is approximately 0.787 inch. The major diameter of the threads 30 at their crests 31 can be approximately 0.256 inch with a minor diameter taken at their root 33 of approximately 0.126 inch. The pitch between adjacent threads 30 at corresponding locations on the crests 31 thereof is approximately 0.1063 inch. With the above-dimensions, the length of the counterbore 50 is approximately 0.24 inch and the length of the counterbore 58 is approximately 0.09 inch corresponding to the lengths of the screw shank wall sections 28b and 28a. The taper provided at the bore section 56 is approximately seven degrees from the axis 47 and the wall section 28d extends for approximately 0.173 inch. The main wall section 28a thus has the greatest length of approximately 0.284 inch. In this manner, the present screw anchors 26 are provided with threads 30 having a good purchase for high holding power thereof while keeping the shank wall thickness to a maximum for providing the screw anchor wall 28 with high strength when screwed into bones 14 as anchors for tensioned cables 22 connected thereto.

The installation procedures of the present bone fixation system 10 utilizing the screw anchors 26 in a spinal column application will next be described. If not already preassembled as by a press-fitting of the plug 54 in the bore 50, the screw anchor 26 is assembled by threading the cable 22 through the throughbore 46 until the plug 54 abuts against the stop shoulder surface 51 therein. After incision to access the spinal column 12 anteriorly thereof, the cable portion 52 is threaded through the cannulated driver 61 for being threaded into the vertebra 14. The driver turns the shank 28 about its axis 47 until it is advanced either in a predetermined predrilled location or by self-tapping until the proximate end 32 is flush or recessed below the bone surface 40. In one preferred application of the present cable bone fixation system 10, it is used as an adjunct to decompression devices such as a cage or cages 66 that are inserted in gap 64 between adjunct vertebra 14a and 14b to be stabilized.

Figure 12:
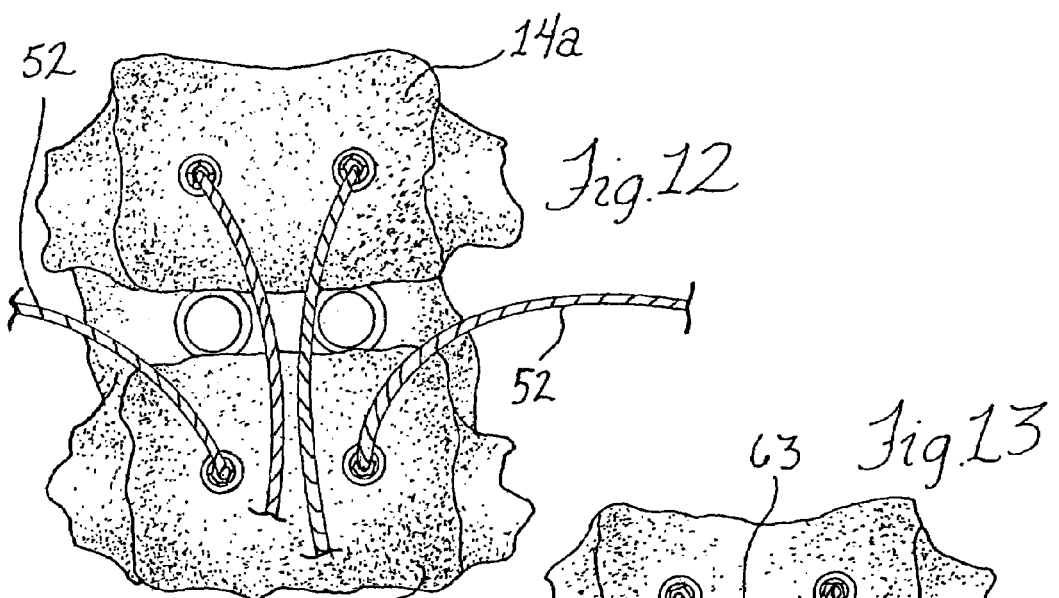
Figure 13:
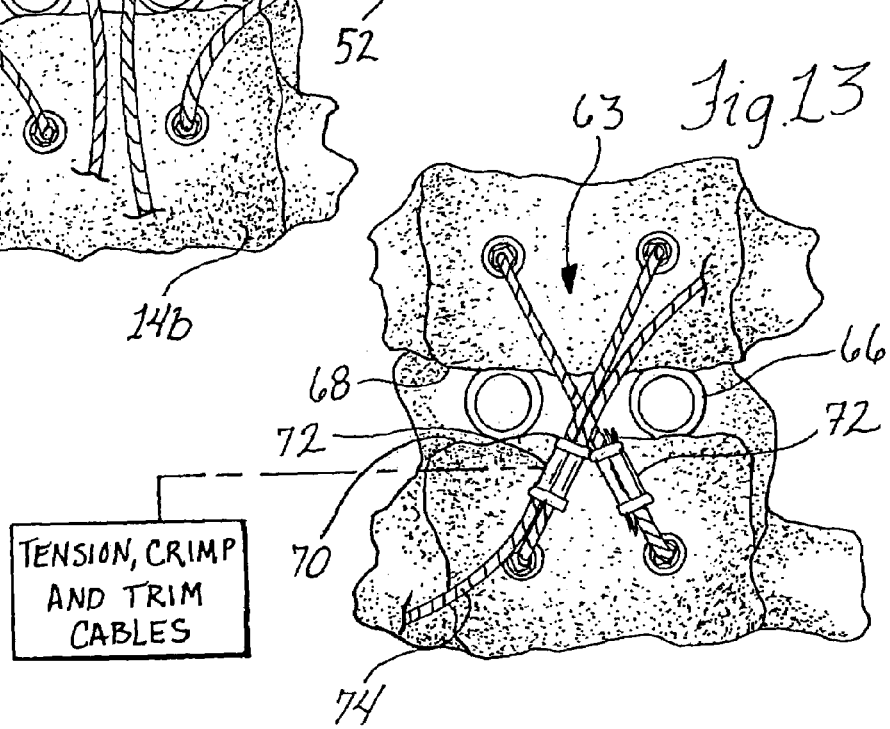

The cages or barrels 66 can have an outer ribbed configuration to provide them with a gripping action on the facing surfaces 68 and 70 of the vertebrae 14a and 14b. To further reduce or resist motion of the vertebrae 14a and 14b that may cause the cages 66 to shift or back out of the vertebrae gap 64, a criss-cross cable pattern 63 is employed. As shown in FIGS. 12 and 13, the pairs of screw anchors 26 are spaced laterally in their respective vertebrae 14a and 14b, to be in vertical alignment, and generally above and below the pair of decompression cages 66. For forming the criss-cross pattern 63, the screw anchors 26 that are offset vertically from each other have their respective cable portions 52 connected together so that the connected cables 22 cross each other approximately midway along the vertical distance that the screw anchor pairs are spaced, which preferably is aligned with the gap 64 between the vertebrae 14a and 14b. In this way, any twisting or torsional forces acting between the vertebrae 14a and 14b is better resisted. As is apparent, twisting in both directions about the spinal column 12 will be resisted by the connected cable pairs that extend transverse to the general vertical orientation of the spine 12.

As can be seen in FIG. 12, the cable portions 52 freely hang from the bones 14a and 14b after their respective screw anchors 26 have been inserted therein. These cable portions 52 are passed through opposite ends of a connector in the form of a generally cylindrical crimp connector 72. To form the criss-cross configuration 63, the cable portions 52 from the vertically offset screw anchors are passed through the crimp connector 72, so that the connected cables cross each other approximately midway along the vertical spacing between the pairs of screw anchors 26 and preferably aligned at the vertebra gap 64, as previously discussed and shown in FIG. 13. Thereafter, crimping and tensioner mechanisms (not shown) are applied to the cylindrical body of the crimp connector 72 either separately or in combination. The tensioner applies an appropriate tension to both free end portions 52 of the cables 22 followed by the crimping tool crimping the connector 72 to retain the tension in the cable portions 52. The crimper and tensioner mechanisms are then removed, and a cable cutter cuts the free projecting portion 74 of the cable portions 52 on each side of the crimp connector 72 with the cut cable portions 74 removed.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

I claim:

1. A system for maintaining positions of bone surfaces fixed relative to each other, the system comprising:
   a first anchor member constructed to be inserted in a bone portion including one of the bone surfaces to be relatively fixed;
   a second anchor member constructed to be inserted in another bone portion including the other bone surface to be relatively fixed;
   a first cable connected to the first anchor member;
   a second cable connected to the second anchor member;
   the first and second anchor members each having an axial bore in which the respective first and second cables extend and are secured with the bores being configured to each include tapered and radiused surface portions against which the respective cables bear to minimize discrete stress points on the cables extending therein and out therefrom with the tapered surface portion being substantially longer than the radiused surface portion;
   a connector between the first and second cables for interconnecting the cables to each other; and
   the first and second anchor members constructed to be substantially fully sunk into the bone portions to minimize space taken up thereby at the location in the body containing the bone portions and disposed on opposite sides of the bone surfaces with the connected cables spanning the surfaces to keep the surfaces fixed relative to each other.

2. The system of claim 1 wherein the anchor members and portions of the cables extending therefrom are generally transversely oriented relative to each other with the cable portions bearing on the bone portions to provide maximum support thereto when connected together.

3. The system of claim 1 wherein the anchor members are headless bone screws that are threaded for substantially their entire length to allow the cables to ride on the bone portions as a bearing surface therefor to minimize wear thereof.

4. The system of claim 1 wherein the connector is a crimp connector with the cables tensioned and crimped in the connector to secure the cables in tension to each other.

5. A system for maintaining positions of bone surfaces fixed relative to each other, the system comprising:
   a first anchor member constructed to be inserted in a bone portion including one of the bone surfaces to be relatively fixed;
   a second anchor member constructed to be inserted in another bone portion including the other bone surface to be relatively fixed;
   a first cable connected to the first anchor member;
   a second cable connected to the second anchor member;
   the first and second anchor members each having an axial bore in which the respective first and second cables extend and are secured with the bores being configured to minimize discrete stress points on the cables extending therein and out therefrom;
   a connector between the first and second cables for interconnecting the cables to each other;
   the first and second anchor members constructed to be substantially fully sunk into the bone portions to minimize space taken up thereby at the location in the body containing the bone portions and disposed on opposite sides of the bone surfaces with the connected cables spanning the surfaces to keep the surfaces fixed relative to each other, wherein the bone portions are vertebrae of a spinal column,
   third and fourth anchor members and connected third and fourth cables, respectively, with the first and third anchor members constructed to be fully sunk into one vertebra and the second and fourth anchor members constructed to be fully sunk into the other vertebra,
   a decompression device constructed to be arranged between the vertebrae for maintaining spacing between facing surfaces of the vertebrae, and
   another connector to allow the cables to be connected to form a criss-cross cable pattern for enhanced stability of the decompression device between the vertebrae and increased resistance to torsional forces on the vertebrae during dynamic motion of the spinal column.

6. A method of stabilizing bone portions relative to each other, the method comprising:
   providing screw anchors and cables attached thereto in axial bores of the screw anchors;
   engaging an internal driver surface of the screw anchors with a correspondingly configured driver;
   threading the screw anchors into predetermined points of insertion therefor on the bone portions until a proximate end of the screw anchors is flush or recessed below the respective bone surfaces;
   flexing the cables in the axial bores against elongate tapered surfaces therein and bending the cables about radiused surfaces at end openings of the axial bores as the cables exit the bores of the screw anchors to minimize discrete stress points on the cables; and
   connecting portions of the cables extending from the screw anchors across the bone portions to be stabilized.

7. A method of stabilizing bone portions relative to each other, the method comprising:
   providing screw anchors and cables attached thereto;
   engaging an internal driver surface of the screw anchors with a correspondingly configured driver;
   threading the screw anchors into predetermined points of insertion therefor on the bone portions until a proximate end of the screw anchors is flush or recessed below the respective bone surfaces; and
   connecting portions of the cables extending from the screw anchors across the bone portions to be stabilized,
   wherein two pairs of screw anchors are threaded into adjacent vertebrae having a decompression device therebetween with one screw anchor pair in each vertebra, and the cable portions are connected to form a criss-cross pattern to resist shifting of the decompression device.

* * * * *